United States Patent
Read et al.

(10) Patent No.: US 6,617,282 B2
(45) Date of Patent: Sep. 9, 2003

(54) PROCESSES FOR PREPARING 3-PHENYL-2, 4(1H, 3H)-PYRIMIDINEDIONES

(75) Inventors: Mark Read, Willoughby, OH (US); Masamitsu Tsukamoto, Mayfield Heights, OH (US); Sandeep Gupta, Concord, OH (US)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

(21) Appl. No.: 09/962,081

(22) Filed: Sep. 26, 2001

(65) Prior Publication Data

US 2003/0096990 A1 May 22, 2003

Related U.S. Application Data

(63) Continuation-in-part of application No. 09/888,426, filed on Jun. 26, 2001, now abandoned.

(51) Int. Cl.[7] .................. C07D 239/54; A01N 43/54
(52) U.S. Cl. .................. 504/243; 544/296; 544/310; 544/312
(58) Field of Search .................. 544/310, 312, 544/296; 504/243

(56) References Cited

FOREIGN PATENT DOCUMENTS

| WO | WO 96/07323 | 3/1996 |
| WO | WO 96/08151 | 3/1996 |
| WO | WO 98/41093 | 9/1998 |

*Primary Examiner*—John M. Ford
(74) *Attorney, Agent, or Firm*—Sughrue Mion, PLLC

(57) ABSTRACT

A process for producing 3-phenyl-2,4(1H,3H)-pyrimidinediones having the general formula I and their salts

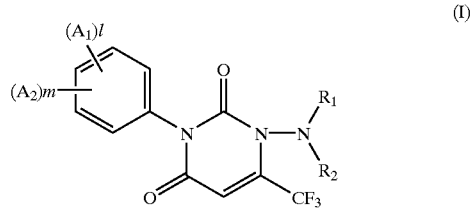

which comprises reacting the isocyanates represented by the general formula (II)

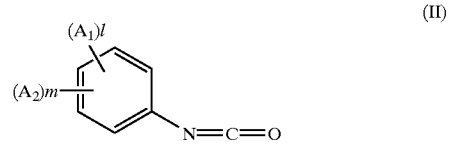

and the substituted hydrazono esters represented by the general formula (III)

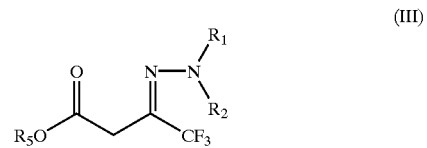

in the presence of a base.

These compounds are useful as herbicides, defoliants and desiccants.

8 Claims, No Drawings

PROCESSES FOR PREPARING 3-PHENYL-2, 4(1H, 3H)-PYRIMIDINEDIONES

This is a Continuation-in-Part of Application No. 09/888,426 filed Jun. 26, 2001, now abandoned.

TECHNICAL FIELD

A class of 3-phenyl-2,4(1H,3H)-pyrimidinediones and compositions containing them as active ingredients are useful as herbicides, defoliants and desiccants.

Background Art

It has been known, that certain 3-phenyl-2,4(1H,3H)-pyrimidinediones are useful in the control of weeds, and they can be prepared by using various processes in the literature; for example WO96/07323, WO96/08151, WO98/41093.

It has also concretely been known in WO98/41093, that the specific 3-phenyl-2,4(1H,3H)-pyrimidinediones can be produced by using the isocyanates and 3-amino or 3-hydrazino-4,4,4-trifluorocrotonate esters.

However, it has not been known therein that they can be produced by using the isocyanates and 3-substituted hydrazino-4,4,4-trifluorocrotonate esters.

Disclosure of the Invention

The need continues for novel and improved herbicidal, defoliant or desiccant compounds, and compositions containing these compounds, and further for industrial preparation process therefor. This invention relates to novel preparation processes of certain 3-phenyl-2,4(1H,3H)-pyrimidinediones represented by the general formula (I) or their salts, some compounds among them and compositions containing said some compounds for herbicides, defoliants or desiccants, and methods of using these compositions.

This invention relates to a process for producing 3-phenyl-2,4(1H,3H)-pyrimidinediones having the general formula (I) and their salts (I)

wherein
- $A_1$ is hydrogen, halogen, cyano, nitro, alkyl, alkenyl, alkynyl, cycloalkyl, cycloalkenyl, cyloalkynyl, cycloalkylalkyl, each being optionally substituted,
- $A_2$ is hydrogen, —$Q_1$—$A_3$ wherein $Q_1$ is O, S, SO, or $SO_2$; $A_3$ is hydrogen or $A_4$ ($A_4$ is alkyl, alkenyl, alkynyl, cycloalkyl, cycloalkenyl, cyloalkynyl, cycloalkylalkyl, aryl, arylalkyl, heterocyclyl, heterocyclicalkyl, each being optionally substituted), —$Q_1$—$CQ_2$—$A_3$ wherein $Q_2$ is O or S, —$Q_1$—$CQ_2$—$Q_2$—$A_3$, —$Q_1$—$CQ_2$—$N(A_3)_2$, —$CQ_2$—$A_3$, —$CQ_2$—$Q_2$—$A_3$, —$CQ_2$—$N(A_3)_2$, —$N(A_3)_2$, —$N(Q_1$—$A_3)_2$, —$N(CQ_2$—$A_3)_2$, —$N(Q_1$—$A_3)$ ($CQ_2$—$A_3$), —$N(CQ_2$—$Q_2$—$A_3)_2$, —$N(A_3)$—$CQ_2$—$N(A_3)_2$, or —$SO_2$—$N(A_3)_2$, each $A_3$ group of $(A_3)_2$ being independently same or different, any two of $(A_1)l$ and $(A_2)m$ groups being optionally combined through a saturated or unsaturated carbon, —$CQ_2$—, and/or hetero O, N, S, SO, or $SO_2$ linkages to form a cyclic ring having up to 12 membered ring, each being optionally substituted,
- l is an integer of 1 to 5, m is an integer of 1 to 3, l+m is an integer of 2 to 5,
- $R_1$ is $A_4$, —$Q_1$—$A_3$, —$Q_1$—$CQ_2$—$A_3$, —$Q_1$—$CQ_2$—$Q_2$—$A_3$, —$Q_1$—$CQ_2$—$N(A_3)_2$, —$CQ_2$—$A_3$, —$CQ_2$—$Q_2$—$A_3$, —$CQ_2$—$N(A_3)_2$, —$N(A_3)_2$, —$N(Q_1$—$A_3)_2$, —$N(CQ_2$—$A_3)_2$, —$N(Q_1$—$A_3)$ ($CQ_2$—$A_3$), —$N(CQ_2$—$Q_2$—$A_3)_2$, —$N(A_3)$—$CQ_2$—$N(A_3)_2$, or —$SO_2$—$N(A_3)_2$, each $A_3$ group of $(A_3)_2$ being independently same or different,
- $R_2$ is hydrogen or $R_1$.
- $R_1$ and $R_2$ groups being optionally combined together with N of $N(R_1)(R_2)$ through a saturated or unsaturated carbon, —$CQ_2$—, and/or hetero O, N, S, SO, or $SO_2$ linkages to form a cyclic ring having up to 12 membered ring, each being optionally substituted, which comprises reacting the isocyanates represented by the general formula (II)

(II)

wherein $A_1$, $A_2$, l and m are as defined above, and the substituted hydrazono esters represented by the general formula (III)

(III)

wherein $R_5$ is $A_4$, $R_1$ and $R_2$ are as defined above, with or without the presence of a base.

DETAILED DESCRIPTION OF THE INVENTION

This invention relates to said process for producing 3-phenyl-2,4(1H,3H)-pyrimidinediones having the general formula (I) and their salts.

Some compounds of the formula (I) may form a salt with an acidic substance or a basic substance. The salt with an acidic substance may be an inorganic acid salt such as hydrochloride, hydrobromide, phosphate, sulfate or nitrate. The salt with a basic substance may be a salt of an inorganic or organic base such as sodium salt, potassium salt, calcium salt, quarternary ammonium salt such as ammonium salt or dimethylamine salt.

The substituents concerning the term of "each being optionally substituted" or "substituted or unsubstituted" in the various definitions of the formulas (I), (I-a) to (I-c), (II), (II-a) to (II-c), (III), (III-a) to (III-c), may include halogen, cyano, nitro, amino, hydroxy, alkyl, haloalkyl, alkoxy, haloalkoxy, alkylthio, alkylsulfonyl, alkylsulfinyl, dialkylaminocarbonyl, alkylsulfonylamino, alkoxycarbonylalkoxy, alkylcarbonylamino, alkoxycarbonylamino, bis-acylamino, aminoacyl, aminohalogenoacyl, or aminoalkylsulfonate. Number of the substituents is one or more, when the substituents are two or more, they are same or different.

The term of "alkyl" by itself or as part of another substituent, means, unless otherwise stated, a straight or branched chain, and can include di- and multi-radicals, having number of carbon atoms designated (i.e. $C_{1-6}$ means one to six carbons). Examples of alkyl groups may include ones with $C_{1-6}$, preferably $C_{1-4}$ such as methyl, ethyl, propyl, butyl, pentyl, or hexyl. The term of "alkenyl", or "alkynyl" by itself or as part of another substituent, means, unless otherwise stated, a straight or branched chain, and can include di- and multi-radicals, having the number of carbon atoms designated (i.e. $C_{2-6}$ means two to six carbons). Examples of alkenyl or alkynyl groups may include ones with $C_{2-6}$, preferably $C_{2-4}$ such as vinyl, propenyl, butenyl, pentenyl, or hexenyl; ethynyl, propynyl, butynyl, pentynyl, or hexynyl. The term of "cycloalkyl", "cycloalkenyl" or "cycloalkynyl" by itself or as part of another substituent, means, unless otherwise stated, cyclic radicals, which may be fully saturated, mono-, or poly-unsaturated, and can include di- and multi-radicals, having the number of carbon atoms designated (i.e. $C_{3-12}$ means three to twelve carbons). Examples of cycloalkyl, cycloalkenyl or cycloalkynyl group may include ones with $C_{3-12}$, preferably $C_{3-9}$, more preferably $C_{3-6}$ such as cyclopropyl, cyclobutyl, cyclopentyl, or cyclohexyl; cyclopropenyl, cyclobutenyl, cyclopentenyl, or cyclohexenyl; cyclopropynyl, cyclobutynyl, cyclopentynyl, or cyclohexynyl.

The term of "acyl" by itself or as part of another substituent, means, unless otherwise stated, a group represented by the formula "—$CQ_2$—$A_4$".

The term of "halogen" by itself or as part of another substituent, means, unless otherwise stated, fluorine, chlorine, bromine, or iodine. For example, haloalkyl or haloalkoxy group constitutes the alkyl or alkoxy and one or more halogen atoms as mentioned above. When the number of halogen atom is two or more, halogen atoms may be independently same or different.

The substituted hydrazono esters may include the compounds of the formulas (111), (111-1), (111-a) to (111-c) and their isomers; for example, the compounds are represented by the general formula (111)

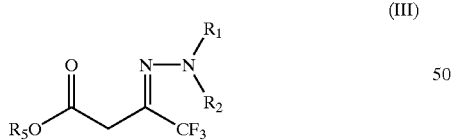

(III)

and their isomers are represented by the general formula (111$_1$)

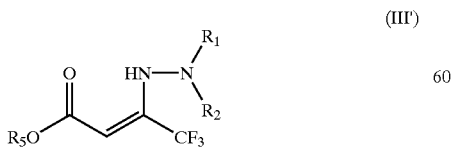

(III')

The bases to be used in the processes of the present invention may include inorganic bases such as alkali metals or alkali earth metals, their hydrides, alkoxides, hydroxides or carbonates; metallic sodium, and alkyl lithiums e.g. butyl lithium lithium hydride, sodium hydride, sodium methoxide, sodium hydroxide, potassium hydroxide, calcium hydroxide, magnesium hydroxide, calcium carbonate; Grignard Reagents such as ($C_{1-6}$) alkyl or aryl magnesium halide such as methyl magnesium bromide, ethyl magnesium bromide, n-propyl magnesium bromide, phenyl magnesium bromide, methyl magnesium chloride, dialkyl magnesium, preferably Grignard Reagents, more preferably methyl magnesium bromide; or an organic base such as mono, di, or trialkylamines or alkanolamines (e.g. monomethylamine, dimethylamine, trimethylamine, triethylamine, triethanolamine etc.), pyridine, lutidine, etc.

1) The preferred processes of the invention are as follows.

A process for producing 3-(3-substituted phenyl)-2,4(1H, 3H)-pyrimidinediones having the general formula (I-a) and their salts

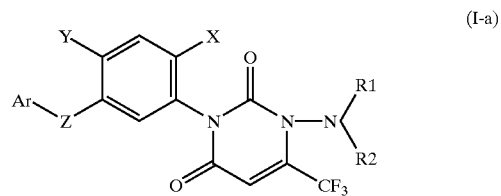

(I-a)

wherein

X, Y are hydrogen, halogen, cyano, nitro, alkyl, alkoxy, cycloalkyl, cycloalkylalkyl or thiocarbamoyl, each being optionally substituted, Z is O, S, SO, $SO_2$ or NR wherein R is alkyl, alkenyl, alkynyl, cycloalkyl, cycloalkylalkyl, each being optionally substituted, Ar is a substituted or unsubstituted 3 to 12 membered cyclic ring, it having optionally one or more saturated or unsaturated carbon, —$CQ_2$—, and/or hetero O, N, S, SO, or $SO_2$ linkages, $R_1$ is $A_4$, —$Q_1$—$A_3$, —$Q_1$—$CQ_2$—$A_3$, —$Q_1$—$CQ_2$—$Q_2$—$A_3$, —$Q_1$—$CQ_2$—N($A_3$)$_2$, —$CQ_2$—$A_3$, —$CQ_2$—$Q_2$—$A_3$, —$CQ_2$—N($A_3$)$_2$, —N($A_3$)$_2$, —N($Q_1$—$A_3$)$_2$, —N($CQ_2$—$A_3$)$_2$, —N($Q_1$—$A_3$)($CQ_2$—$A_3$), —N($CQ_2$—$Q_2$—$A_3$)$_2$, —N($A_3$)—$CQ_2$—N($A_3$)$_2$ or —$SO_2$—N($A_3$)$_2$, each $A_3$ group of ($A_3$)$_2$ being independently same or different, $R_2$ is hydrogen or $R_1$.

$R_1$ and $R_2$ groups being optionally combined together with N of N($R_1$)($R_2$) through a saturated or unsaturated carbon, —$CQ_2$—, and/or hetero O, N, S, SO, or $SO_2$ linkages to form a cyclic ring having up to 12 membered ring, each being optionally substituted, which comprises reacting the isocyanates represented by the general formula (II-a)

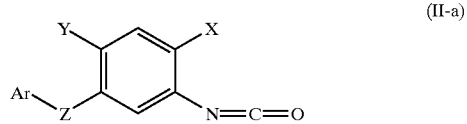

(II-a)

wherein Ar, X, Y, and Z are as defined above, and the substituted hydrazono esters represented by the general formula (III-a)

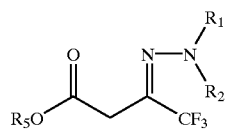
(III-a)

wherein $R_5$ is $A_4$, with or without the presence of a base.

2) The more preferred processes of the invention are as follows.

A process for producing 3-(3-substituted phenyl)-2,4(1H, 3H)-pyrimidinediones having the general formula (I-b) and their salts (I-b)

wherein

X, Y are hydrogen, halogen, cyano, nitro, alkyl, alkoxy, cycloalkyl, cycloalkylalkyl, or thiocarbamoyl, each being optionally substituted, Z is O, S or NR wherein R is alkyl, alkenyl, alkynyl, cycloalkyl, each being optionally substituted, Ar is a substituted or unsubstituted aryl or heteroaryl, $R_1$ is a substituted or unsubstituted protective group, $R_2$ is hydrogen, alkyl, alkenyl, alkynyl, aryl or protective group, each being optionally substituted, $R_1$ and $R_2$ groups being optionally combined together with N of $N(R_1)(R_2)$ through a saturated or unsaturated carbon, —$CQ_2$—, and/or hetero O, N,S, SO, or $SO_2$ linkages to form a cyclic ring having up to 12 membered ring, each being optionally substituted, which comprises reacting the isocyanates represented by the general formula (II-b)

(II-b)

wherein Ar, X, Y, and Z are as defined above, and the substituted hydrazono esters represented by the general formula (III-b)

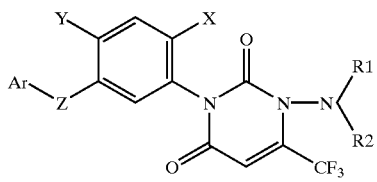
(III-b)

wherein $R_5$ is $A_4$, with or without the presence of a base.

3) The most preferred processes of the invention are as follows.

A process for producing 3-(3-substituted phenyl)-2,4(1H, 3H)-pyrimidinediones having the general formula (I-c) and their salts (I-c)

wherein

X, Y are hydrogen, halogen, cyano, nitro, alkyl, alkoxy, cycloalkyl, cycloalkylalkyl or thiocarbamoyl, each being optionally substituted, Z is O, S, SO, $SO_2$ or NR wherein R is alkyl, alkenyl, alkynyl, cycloalkyl, cycloalkylalkyl, each being optionally substituted, Ar is a substituted or unsubstituted 3 to 12 membered cyclic ring, it having optionally one or more saturated or unsaturated carbon, —$CQ_2$—, and/or hetero O, N, S, SO, or $SO_2$ linkages, $R_3$ is $A_4$, —$Q_1$—$A_3$, —$Q_1$—$CQ_2$—$A_3$, —$Q_1$—$CQ_2$—$Q_2$—$A_3$, —$Q_1$—$CQ_2$—$N(A_3)_2$, —$CQ_2$—$A_3$, —$CQ_2$—$Q_2$—$A_3$, —$CQ_2$—$N(A_3)_2$, —$N(A_3)_2$, —$N(Q_1$—$A_3)_2$, —$N(CQ_2$—$A_3)_2$, —$N(Q_1$—$A_3)(CQ_2$—$A_3)$, —$N(CQ_2$—$Q_2$—$A_3)_2$, —$N(A_3)$—$CQ_2$—$N(A_3)_2$ or —$SO_2$—$N(A_3)_2$, each $A_3$ group of $(A_3)_2$ being independently same or different, $R_4$ is hydrogen or $R_3$, $R_3$ and $R_4$ groups being optionally combined together with C of =$C(R_3)(R_4)$ through a saturated or unsaturated carbon, —$CQ_2$—, and/or hetero O, N,S, SO, or $SO_2$ linkages to form a cyclic ring having up to 12 membered ring, each being optionally substituted, which comprises reacting the isocyanates represented by the general formula (II-c)

(II-c)

and the substituted hydrazono esters represented by the general formula (III-c)

(III-c)

wherein $R_5$ is $A_4$, with or without the presence of a base.

The term of "aryl" by itself or as part of another substituent, means, unless otherwise stated, aromatic ring in the various definitions of the formulas (I), (I-a) to (I-c), (II), (II-a) to (II-c), (III), (III-a) to (III-c), may include may be a six or twelve membered ring such as phenyl or naphthyl, and the heteroaryl may be five to twelve, or preferably five to six membered ring having at least one hetero atom of nitrogen, oxygen or sulfur, and for example may be pyridyl, pyrimidyl, pyridazinyl, triazolyl, thiazolyl or isothiazolyl, etc.

The protective groups in the definitions of $R_1$ to $R_4$ for the general formulas (I), (I-a) to (I-c), (III), (III-a) to (III-c), may be certain groups provided by conventional reactions for introducing one or more protective groups to an amino group of certain organic compounds using reaction reagents having the protective group. For example, they may include acyl, carbamoyl, sulfonyl or sulfamoyl. Substituents for each of acyl, carbamoyl, sulfonyl or sulfamoyl group, are selected from the group of acceptable substituents as described above: e.g. formyl, acetyl, propionyl, cyclohaxanoyl, propioloyl, crotonyl, acryloyl, methacryloyl, benzoyl, phenylacetyl, anisoyl, toluoxyl (o, m, p), salicyloyl (o, m, p), carbamoyl, dimethylcarbamoyl, oxamoyl, sulfonyl, tosyl (o, m, p), phenylsulfonyl, sulfamoyl, phenylsulfamoyl, etc.

The cyclic ring having up to 12 membered ring in the definitions of $R_1$ to $R_2$ may include a saturated or unsaturated cyclic ring containing the N of $N(R_1)(R_2)$ in the general formulas (I), (I-a) to (I-b), (III), (III-a) to (II-b) as well as from zero to four hetero atoms selected from the group consisting of O, N, S, SO, or $SO_2$, and the ring optionally substituted by one or more groups of said acceptable substituents: e.g. piperidino, morpholino, terephthalino, 3,4,5, 6-tetrahydrophtharino etc. Further, said cyclic ring in the definition of $R_1$ and $R_2$ may also include ones having the general formulas (I-c) and (III-c) ; —N=$C(R_3)(R_4)$ wherein $R_3$ and $R_4$ are hydrogen, substituted or unsubstituted alkyl, alkenyl, alkynyl, aryl or a protective group; or $R_3$ and $R_4$ may combine together with the carbon atom of =$C(R_3)(R_4)$ to form a substituted or unsubstituted cyclic ring. Such cyclic ring may include a saturated or unsaturated cyclic ring containing from zero to four hetero atoms selected from nitrogen, oxygen and sulfur, and the ring optionally substituted by one or more groups of said acceptable substituents: e.g. methylethylidene, methylpropylidene, benzylidene, phenylbenzylidene, cyclopentylidene, etc.

Among the compounds of the general formula (I), the 3-(3-substituted phenyl)-2,4(1H,3H)-pyrimidinediones of this invention having the general formula (I-c) are novel.

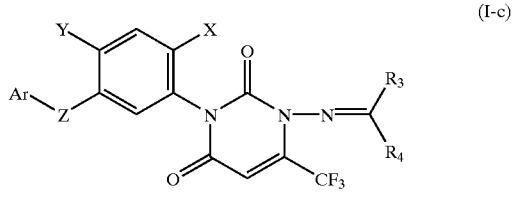

wherein X, Y, Z, Ar, $R_3$ and $R_4$ are as described above.

The preferred formula (I-c) compounds of this invention are those;
wherein
X, Y are halogen;
Z is oxygen or sulfur;
Ar is pyridyl, pyrimidyl, triazolyl, thiazolyl, isothiazolyl, or phenyl, or pyridyl, pyrimidyl, triazolyl, thiazolyl, isothiazolyl, or phenyl substituted with up to five substituents independently selected the from group consisting of bromo, chloro, fluoro, iodo, $(C_1–C_4)$alkyl, halo$(C_{1-4})$alkyl, $(C_{1-4})$alkoxy, $(C_{1-4})$alkylthio, halo$(C_{1-4})$alkoxy, $(C_{1-4})$alkylsulfonyl, $(C_1–C_3)$ alkylsulfinyl, di$(C_{1-4})$alkylaminocarbonyl, cyano, nitro, $(C_{1-4})$alkylsulfonylamino, $(C_{1-4})$alkoxycarbonyl $(C_{1-4})$alkoxy, and $(C_{1-4})$alkoxycarbonylamino.

The more preferred formula (I-c) compounds of this invention are those;
wherein
X is fluorine;
Y is chlorine;
Z is oxygen or sulfur;
Ar is 2-pyridyl, 3-pyridyl, 4-pyridyl, 3-bromo-2-pyridyl, 5-bromo-2-pyridyl, 6-bromo-2-pyridyl, 3-chloro-2-pyridyl, 5-chloro-2-pyridyl, 6-chloro-2-pyridyl, 3-fluoro-2-pyridyl, 5-fluoro-2-pyridyl, 6-fluoro-2-pyridyl, 3-cyano-2-pyridyl, 5-cyano-2-pyridyl, 6-cyano-2-pyridyl, 3-nitro-2-pyridyl, 5-nitro-2-pyridyl, 6-nitro-2-pyridyl, 3-trifluoromethyl-2-pyridyl, 4-trifluoromethyl-2-pyridyl, 5-trifluoromethyl-2-pyridyl, 6-trifluoromethyl-2-pyridyl, 3-dimethylaminocarbonyl-2-pyridyl, 3-methylsulfonyl-2-pyridyl, 3-isopropylsulfonyl-2-pyridyl, 6-chloro-3-trifluoromethyl-2-pyridyl, 3,5,6-trifluoropyridyl, 2-pyrimidyl, 4-pyrimidyl, 5-bromo-2-pyrimidyl, 4-chloro-2-pyrimidyl, 4-trifluoromethyl-2-pyrimidyl, 4,6-dimethoxy-2-pyrimidyl, 2,6-dimethoxy-4-pyrimidyl, 4,6-dimethoxy-2-triazinyl, phenyl, 2-iodophenyl, 2-trifluoromethoxyphenyl, 2-nitrophenyl, 4-nitrophenyl, 4-methylsulfonylaminophenyl, 4-(1-ethoxycarbonylethoxy)phenyl, 2-cyanophenyl, 2-cyano-3-fluorophenyl, 2-cyano-4-fluorophenyl, 2-cyano-4-nitrophenyl, 4-nitro-2-trifluoromethylphenyl, 4-acetylamino-2-trifluoromethylphenyl, 4-(1-ethoxycarbonylethoxy)-2-nitrophenyl, 5-chloro-4-(1-ethoxycarbonylethoxy)-2-nitrophenyl, 3-methyl-4-nitro-5-isothiazolyl, or 5-nitro-2-thiazolyl.

The compounds of this invention having said general formula I can be prepared by the reaction scheme mentioned in Process (1).

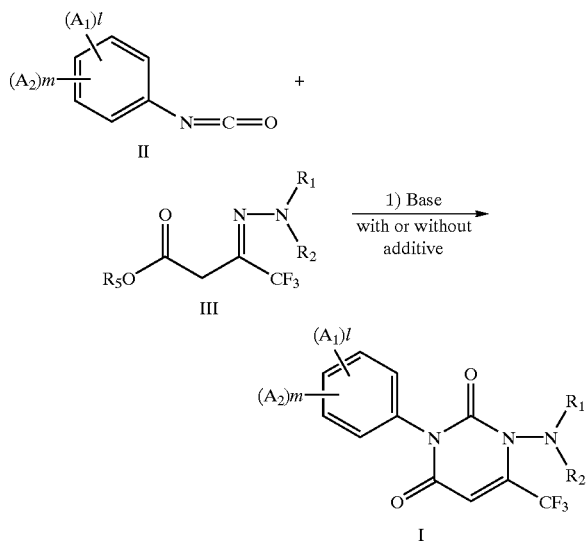

Process (1)

The reaction is carried out by mixing the isocyanates (II) and the hydrazono-esters (III) in the presence of bases, usually by the first step of mixing the compounds III and bases, and then the second step of adding the isocyanates II to thus obtained mixture with or without solvents.

The bases to be used in the processes of the present invention are as described above, and are employed in appropriate methods.

The solvents may include ethers such as dimethyl ether, diethyl ether, methyl ethyl ether, tetrahydrofuran; aromatic hydrocarbons such as benzene, toluene; aliphatic hydrocarbons such as pentane, hexane, preferably dimethyl or diethyl ether, tetrahydrofuran, benzene, toluene, pentane and hexane, more preferably tetrahydrofuran.

The additive such as inorganic or organic salts of metal may be used in the process (1). They may include ones of metal atom selected from the group consisting of Mg, Al, B, Zn, Ti and lanthanides (e.g. $MgCl_2$, $MgI_2$, $AlCl_3$, $BF_3$, $TiCl_4$).

The reaction may be conducted usually by using 0.5–2.0 moles of the isocyanates (II) and 0.5–3.0 moles of the bases based on one mole of the compounds (III), preferably 0.7–1.5 moles of the isocyanates (II) and 0.7–2.0 moles of the bases based thereon, and under an inert atmosphere such as nitrogen gas or argon gas.

The reaction is usually conducted at a temperature of −110° C. to 150° C. and for a period of 1 minute to 5 hours, preferably at a temperature of −78° C. to 25° C. and for a period of 5 minutes to 1 hour.

The reaction products are subjected to the conventional work-up treatments such as quenching, extracting and drying steps, for example, mixing them with water, extracting with suitable organic solvents and drying to obtain the aimed compounds having said general formula (I).

The intermediates II may be prepared by the methods as described in WO98/41093 or their analogous processes. For example, the intermediates (II-a) can be prepared by the following reaction scheme as mentioned in Process (2).

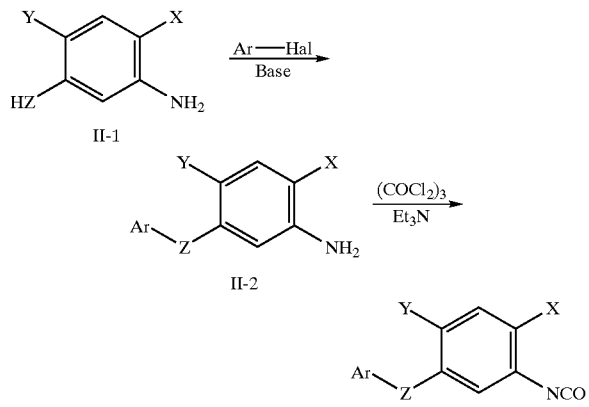

Process (2)

Process (2) is carried out by two stages. The first step is carried out by using the reactions of aminophenols (II-1) with aryl halides or heteroaryl halides with or without solvents. The solvents may include acetonitrile, tetrahydroftiran, dimethyl imidazolidine, dimethylsulfoxide, hexamethylphosphoric triamide, N,N-dimethylformamide, acetone, butan-2-one, benzene, toluene or xylene, in the presence of bases such as potassium carbonate, sodium carbonate, potassium hydroxide, sodium hydroxide, potassium t-butoxide, potassium fluoride, or sodium hydride. Catalysts may or may not be used. Such catalysts include copper(1)chloride, copper(1)oxide, copper, copper(1) alkoxides, alkyl cuprates, palladium(0), tetrabutylammonium halides, or 8-quinolinol. The reaction temperature is usually from 0° C. to 250° C., preferably from 20° C. to 120° C. The reaction time is from 1 to 12 hours, preferably from 2 to 6 hours.

The diaryl ethers (II-2) may also be prepared by treatment of aminophenols (II-1) with aryl-lead tricarboxylates, triphenylbismuth-diacetate, triphenylbismuth-trifluoroacetate or diphenyliodonium halides in the presence of solvents such as benzene, toluene, dichloromethane, dichloroethane, chloroform or water, with or without catalysts such as copper, or transition metals.

The reaction may be conducted usually by using 0.1–10 moles of the Ar-Hal based on the aminophenol. The temperature is usually from 0° C. to the reflux temperature of the mixture, and the reaction time from 10 minutes to 72 hours. The temperature is preferably from 20° C. to the reflux temperature of the mixture, and the time preferably 2 to 6 hours.

The second step requires treatment of the amines (II-2) with phosgene or triphosgene in solvents such as hexane, heptane, benzene, toluene, xylene, or ethyl acetate. The reaction temperature is usually from 0° C. to the reflux temperature of the mixture, preferably at the reflux temperature thereof. The reaction time is usually from 30 minutes to 6 hours, preferably from 2 to 3 hours.

The other intermediates (III) can be prepared by the methods mentioned in Process (3).

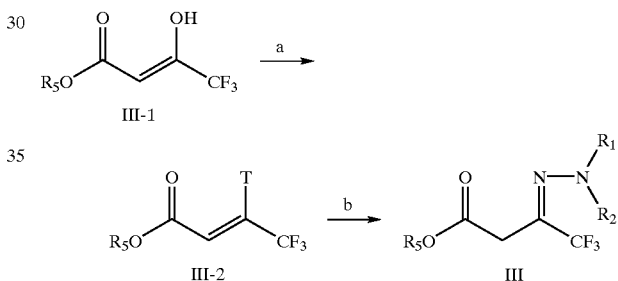

Process (3)

wherein $R_5$ is as described above, T is halogen, ether or ester forming residue (e.g. acyloxy, alkoxy, alkenyloxy, alkynyloxy, aryloxy, sulfonyloxy).

Process (3) is also usually carried out by two steps.

The first step is carried out by using the reactions of alkali metal (e.g. lithium, sodium, potassium) esters of 4,4,4-trifluoroacetoacetate (III-1) with a halogenating agent such as phosphorus oxychloride, phosphorus pentachloride, thionyl chloride, etc., and reagents for elimination reactions such as triflic acid, its halide, anhydride or ester with or without solvents. The reaction may be conducted usually by using 0.3–3.0 moles of the reagents thereof based on one mole of the alkali metal esters of 4,4,4-trifluoroacetoacetate (III-1). The solvents may include ethers such as dimethyl ether, diethyl ether, methyl ethyl ether, dioxane, tetrahydrofuran; aromatic hydrocarbons such as benzene, toluene, xylene; aliphatic hydrocarbons such as hexane, or N,N-dimethylformamide, dimethylsulfoxide, preferably dimethyl or diethyl ether. The reaction temperature is usually from −20° C. to 100° C., preferably from −10° C. to 25° C. The reaction time is from 0.1 to 12 hours, preferably from 0.5 to 2 hours.

The second step is carried out by using the reaction of 2-butenoic acid, 4,4,4-trifluoro-3-O-substituted, esters (III- 2) and substituted hydrazines with or without solvents and bases. Examples of substituted hydrazines may include ones prepared by reactions of hydrazine with ketones having $R_1$—CO—$R_2$ (wherein $R_1$ and $R_2$ are as defined above.) (See. Day, A. C., Whiting, M. C. Organic Syntheses, Coll. Vol. VI, 10.), or by reactions of hydrazine with reaction reagents for conventional reactions for introducing one or more radicals including protective groups to an amino group of certain organic compounds.

The reaction proceeds without any solvents, but is normally accelerated by employing solvents.

Further reaction requires solvents such as aliphatic hydrocarbons e,g, hexane, heptane, ligroin and petroleum ether, aromatic hydrocarbons such as benzene, toluene, xylene, and chlorobenzene, halogenated hydrocarbons such as chloroform and methylene chloride, and the bases of inorganic bases such as potassium carbonate, sodium carbonate, potassium hydroxide, sodium hydroxide, or sodium hydride, or organic amines such as pyridine, triethylamine, diisopropylethylamine, DBU, DBN.

The reaction may be conducted usually by using 0.3–5 moles of the substituted hydrazines based on one mole of the 2-butenoic acid, 4,4,4-trifluoro-3-[[(trifluoromethyl) sulfonyl]oxy]-, esters (III-2).

The reaction temperature is usually from −30° C. to 150° C., preferably from 0° C. to 75° C. The reaction time requires normally from 30 minutes to 20 hours, preferably from 60 minutes to 12 hours.

The intermediates (III) can be also prepared sometimes directly by the methods mentioned below.

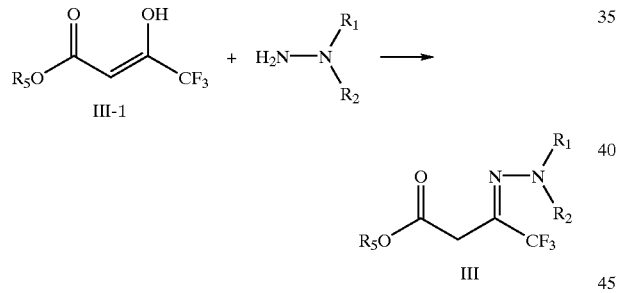

The process is also carried out under the same or analogous conditions as described in Process (3).

Further the compounds of the general formulas (I), (I-a), and (I-b) can be optionally applied to the reactions for changing the group; —N($R_1$)($R_2$) in the chemical structure of the general formulas (I), (I-a), and (I-b) to the amino group; —$NH_2$. Preferably, the compounds having —N=C ($R_3$)($R_4$) group in the general formula (I-c) can be changed into the compounds having the amino group; —$NH_2$ For example, the reaction is carried out by reacting compounds of the general formulas (I), and (I-a) to (I-c) with an aqueous solution of mineral acid such as hydrochloric acid in the presence of alcohol such as methanol at a temperature of from 0° C. to 150° C., usually under a reflux condition. The compounds obtained are also useful as herbicides, defoliants or desiccants, particularly herbicides for controlling undesired weeds in crop land.

The examples according to the present invention will now be illustrated as follows.

EXAMPLES

Example 1

Preparation of ethyl 4,4,4-trifluoro-3-[[(trifluoromethyl)sulfonyl]oxy]-(2Z)-2-butenoate (Compound III-2)

To a solution of sodium ethyl 4,4,4-trifluoroacetoacetate in anhydrous diethyl ether, prepared from ethyl 4,4,4-trifluoroacetoacetate (50.6 g, 0.27 mol) and sodium hydride (60% dispersion in oil, 12.1 g, 0.30 mol) in ether, was added triflic anhydride (85.5 g, 0.30 mol) at 0° C. The reaction was warmed to room temperature for 30 minutes, filtered through Celite, and concentrated under reduced pressure. Distillation of the residue (90–105° C., 50–60 mm Hg) afforded 74.3 g (86%) of a light yellow oil. $H^1$ ($CDCl_3$): δ1.36 (t, J=7.15 Hz, 3H), 4.36 (q, J=7.14 Hz, 2H), 6.54 (s, 1H).

Example 2

Preparation of ethyl 4,4,4-trifluoro-(3Z)-3-[(1-methylethylidene)hydrazono]-butanoate (Compound No. III)

To a solution of acetone hydrazine (1.78 g, 24.7 mmol) and triethyl amine (3.40 mL, 24.4 mmol) in anhydrous methylene chloride was added compound III-2 (7.7 g, 24.4 mmol) in methylene chloride at 0° C. The reaction was warmed to room temperature overnight, quenched with 50 mL water, and the phases separated. The aqueous phase was extracted with methylene chloride (2×100 mL), dried over anhydrous sodium sulfate, and concentrated to give a yellow oil. Chromatography (20% ethyl acetate/hexane) afforded 3.64 g (62.7%) of a yellow oil. $H^1$ ($CDCl_3$): δ1.25 (t, J=7.14 Hz, 3H), 1.94 (s, 3H), 2.06 (s, 3H), 3.54 (s, 2H), 4.14 (q, J=7.14 Hz, 2H).

Example 3

Preparation of 3-[4-hloro-2-fluoro-5-(2-nitrophenoxy)phenyl]-1-[(1-methylethylidene)amino]-6-(trifluoromethyl)-2,4(1H,3H)-pyrimidinedione (Compound No. B)

A 3M solution of methylmagnesium bromide (2.8 mL, 8.4 mmol) was added drop-wise to a solution of compound III (1.80 g, 7.6 mmol) in anhydrous THF at 0° C. under a nitrogen atmosphere. The reaction was stirred for twenty minutes followed by the addition of 4-chloro-2-fluoro-5-(2-nitrophenoxy)phenyl isocyanate(2.56 g, 8.3 mmol) in anhydrous THF at 0° C. The reaction was warmed to room temperature, quenched with saturated ammonium chloride, and extracted with ethyl acetate (3×50 mL). The combined organic layers were dried over anhydrous sodium sulfate and concentrated. Chromatography (20% ethyl acetate/hexane) of the residue afforded 0.48 g (12.7%) of a white solid. $H^1$ ($CDCl_3$): δ1.97 (s, 3H), 2.26 (s, 3H), 6.34 (s, 1H), 6.93 (d, J=8.35 Hz, 1H), 7.07 (d, J=6.52 Hz, 1H), 7.23 (dt, J=7.38, 1.02 Hz, 1H), 7.42 (d, J=8.82 Hz, 1H), 7.52 (dt, J=8.15, 1.67 Hz, 1H), 7.98 (dd, J=8.14, 1.59 Hz, 1H).

Example 4

Preparation of 1-amino-3-[4-chloro-2-fluoro-5-(2-nitrophenoxy)phenyl]-6-(trifluoromethyl)-2,4(1H,3H)-pyrimidinedione A suspension of compound No.B (0.300 g, 0.60 mol), 1 N HCl (3.0 mL,), and methanol (3.0 mL) was heated to refluxed for 2 hours. The reaction was cooled to room temperature, partitioned between water and ethyl acetate, and the phases separated. The aqueous phase was extracted ethyl acetate (3×50 mL) and concentrated. Chromatography (20% ethyl acetate/hexane) of the residue afforded 0.12 g (43.5%) of a white solid. H$^1$ (CDCl$_3$): δ, 4.58 (bs, 2H), 6.25 (s, 1H), 6.94 (dd, J=8.38, 1.13 Hz, 1H), 7.03 (d, J=6.52 Hz, 1H), 7.24 (dt, J=7.29, 1.22 Hz, 1H), 7.43 (d, J=8.83 Hz, 1H), 7.53 (dt, J=7.12, 1.69 Hz, 1H), 7.97 (dd, J=8.15, 1.65 Hz, 1H).

Some of the compounds of the present invention which may be produced by methods as described above are shown in Table 1.

Examples of Formula (I-c)

TABLE 1

(I-c)

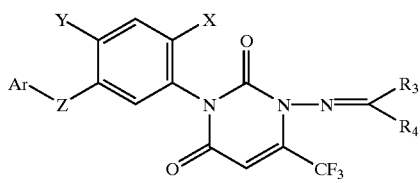

| Compd. No. | Ar | X | Y | Z | R$_3$ | R$_4$ | Physical property |
|---|---|---|---|---|---|---|---|
| A | phenyl | F | Cl | O | CH$_3$ | CH$_3$ | |
| B | 2-nitrophenyl | F | Cl | O | CH$_3$ | CH$_3$ | mp 173–176° C. |
| C | 3-nitro-2-pyridyl | F | Cl | O | CH$_3$ | CH$_3$ | |
| D | 6-fluoro-2-pyridyl | F | Cl | O | CH$_3$ | CH$_3$ | |
| E | 2-nitrophenyl | F | Cl | O | —(CH$_2$)$_4$— | | |
| F | pyrimidyl | F | Cl | O | CH$_3$ | CH$_3$ | |
| G | pyrimidyl | F | Cl | O | —(CH$_2$)$_4$— | | |
| H | phenyl | F | Cl | O | Ethyl | CH$_3$ | |
| I | phenyl | F | Cl | O | phenyl | H | |
| J | pyrimidyl | F | Cl | O | H | H | |
| L | pyrimidyl | H | CN | O | CH$_3$ | CH$_3$ | |
| M | 2-pyridyl | F | Cl | S | phenyl | H | |
| N | 3-cyanophenyl | F | Cl | S | phenyl | phenyl | |

The compounds represented by the general formula (I-c) of the present invention exhibit excellent herbicidal effects when used as active ingredients (a.i.) of herbicides, defoliants or desiccants. The herbicides can sometimes be used for wide ranges of applications, for example on crop lands such as paddy fields, upland farms, orchards and mulberry fields, and non-crop lands such as forests, farm roads, playgrounds, and factory sites. The application methods may be suitably selected for soil treatment applications and foliar applications. The defoliants or desiccants can sometimes be used for wide ranges of applications, for example on crop lands such as cotton, potato, grape and the like.

The compounds of the present invention are capable of controlling noxious weeds including grass (gramineae) such as barnyardgrass (*Echinochloa crus-galli*), large crabgrass (*Digitaria sanguinalis*), green foxtail (*Setaria viridis*), goosegrass (*Eleusine indica* L.), wild oat (*Avena fatua* L.), Johnsongrass (*Sorghum halepense*), quackgrass (*Agropyron repens*), alexandergrass (*Brachiaria plantaginea*), paragrass (*Panicum purpurascen*), sprangletop (*Leptochloa chinensis*) and red sprangletop (*Leptochloapanicea*); sedges (or Cyperaceae) such as rice flatsedge (*Cyperus iria* L.), purple nutsedge (*Cyperus rotundus* L.), Japanese bulrush (*Scirpus Juncoides*), flatsedge (*Cyperus serotinus*), small-flower umbrellaplant (*Cyperus difformis*), slender spikerush (*Eleocharis acicularis*), and water chestnut (*Eleocharis kuroguwai*); alismataceae such as Japanese ribbon wapato (*Sagittaria pygmaea*), arrow-head (*Sagittaria trifolia*) and narrowleaf waterplantain (*Alisma canaliculatum*); pontederiaceae such as monochoria (*Monochoria vaginalis*) and monochoria species (*Monochoria korsakowii*); scrophulariaceae such as false pimpernel (*Lindernia pyxidaria*) and abunome (*Dopatrium Junceum*); lytiuaceae such as toothcup (*Rotala indica*) and red stem (*Ammannia multiflora*); and broadleaves such as redroot pigweed (*Amaranthus retroflexus*), velvetleaf (*Abutilon theophrasti*), morningglory (*Ipomoea hederacea*), lambsquarters (*Chenopodium album*), prickly sida (*Sida spinosa* L.), common purslane (*Portulaca oleracea* L.), slender amaranth (*Amaranthus viridis* L.), sicklepod (*Cassia obtusifolia*), black nightshade (*Solanum nigrum* L.), pale smartweed (*Polygonum lapathifolium* L.), common chickweed (*Stellaria media* L.), common cocklebur (*Xanthium strumarium* L.), flexuous bittercress (*Cardamine flexuosa* WITH.), henbit (*Lamium amplexicaule* L.) and threeseeded copperleaf (*Acalypha australis* L.). Accordingly, they are useful for controlling noxious weeds non-selectively or selectively in the cultivation of a crop plant such as corn (*Zea mays* L.), soybean (*Glycine max* Merr.), cotton (*Gossypium* spp.), wheat (*Triticum* spp.), rice (*Oryza sativa* L.), barley (*Hordeum vulgare* L.), oat (*Avena sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), Japanese lawngrass (*Zoysia Japonica stend*), peanut (*Arachis hypogaea* L.) or flax (*Linum usitatissimum* L.).

For use as herbicides, the active ingredients of this invention are formulated into herbicidal compositions by mixing herbicidally active amounts of them with inert ingredients known to the art to facilitate either the suspension, dissolution or emulsification of the active ingredients for the desired uses. The type of formulation prepared recognizes the facts that formulation, crop and use pattern all can influence the activity and utility of the active ingredients in a particular uses. Thus for agricultural use, the present herbicidal compounds may be formulated as water dispersible granules, granules for direct application to soils, water soluble concentrates, wettable powders, dusts, solutions, emulsifiable concentrates (EC), microemulsion, suspoemulsion, invert emulsion or other types of formulations, depending on the desired weed targets, crops and application methods.

These herbicidal formulations may be applied to the target area (where suppression of unwanted vegetation is the objective) as dusts, granules or water or solvent diluted sprays. These formulations may contain as little as 0.1% to as much as 97% active ingredients by weight.

Dusts are admixtures of the active ingredients with finely ground materials such as clays (some examples include kaolin and montmorillonite clays), talc, granite dust or other organic or inorganic solids which act as dispersants and carriers for the active ingredients; these finely ground materials have an average particle size of less than 50 microns. A typical dust formulation will contain 1% active ingredient and 99% carrier.

Wettable powders are composed of finely ground particles which disperse rapidly in water or other spray carriers. Typical carriers include kaolin clays, Fullers earth, silicas and other absorbent, wettable inorganic materials. Wettable powders can be prepared to contain from 1 to 90% active ingredient, depending on the desired use pattern and the absorbability of the carrier. Wettable powders typically contain wetting or dispersing agents to assist dispersion in water or other carriers.

Water dispersible granules are granulated solids that freely disperse when mixed in water. This formulation typically consists of the active ingredient (0.1% to 95% active ingredient), a wetting agent (1–15% by weight), a dispersing agent (1 to 15% by weight) and an inert carrier (1–95% by weight). Water dispersible granules can be formed by mixing the ingredients intimately then adding a small amount of water on a rotating disc (said mechanism is commercially available) and collecting the agglomerated granules. Alternatively, the mixture of ingredients may be mixed with an optimal amount of liquid (water or other liquid) and passed through an extruder (said mechanism is commercially available) equipped with passages which allow for the formation of small extruded granules. Alternatively, the mixture of ingredients can be granulated using a high speed mixer (said mechanism is commercially available) by adding a small amount of liquid and mixing at high speeds to affect agglomeration. Alternatively, the mixture of ingredients can be dispersed in water and dried by spraying the dispersion through a heated nozzle in a process known as spray drying (spray drying equipment is commercially available). After granulation the moisture content of granules is adjusted to an optimal level (generally less than 5%) and the product is sized to the desired mesh size.

Granules are granulated solids that do not disperse readily in water, but instead maintain their physical structure when applied to the soil using a dry granule applicator. These granulated solids may be made of clay, vegetable material such as corn cob grits, agglomerated silicas or other agglomerated organic or inorganic materials or compounds such as calcium sulfate. The formulation typically consists of the active ingredient (1 to 20%) dispersed on or absorbed into the granule. The granule may be produced by intimately mixing the active ingredient with the granules with or without a sticking agent to facilitate adhesion of the active ingredient to the granule surface, or by dissolving the active ingredient in a solvent, spraying the dissolved active ingredient and solvent onto the granule then drying to remove the solvent. Granular formulations are useful where in-furrow or banded application is desired.

Emulsifiable concentrates (EC) are homogeneous liquids composed of a solvent or mixture of solvents such as xylenes, heavy aromatic naphthas, isophorone or other proprietary commercial compositions derived from petroleum distillates, the active ingredient and an emulsifying agent or agents. For herbicidal use, the EC is added to water (or other spray carrier) and applied as a spray to the target area. The composition of an EC formulation can contain 0.1% to 95% active ingredient, 5 to 95% solvent or solvent mixture and 1 to 20% emulsifying agent or mixture of emulsifying agents.

Suspension concentrate (also known as flowable) formulations are liquid formulations consisting of a finely ground suspension of the active ingredient in a carrier, typically water or a non-aqueous carrier such as an oil. Suspension concentrates typically contain the active ingredient (5 to 50% by weight), carrier, wetting agent, dispersing agent, anti-freeze, viscosity modifiers and pH modifiers. For application, suspension concentrates are typically diluted with water and sprayed on the target area.

Solution concentrates are solutions of the active ingredient (1 to 70%) in solvents which have sufficient solvency to dissolve the desired amount of active ingredient. Because they are simple solutions without other inert ingredients such as wetting agents, additional additives are usually added to the spray tank mix before spraying to facilitate proper application.

Microemulsions are solutions consisting of the active ingredient (1 to 30%) dissolved in a surfactant or emulsifier, without any additional solvents. There are no additional solvents added to this formulation. Microemulsions are particularly useful when a low odor formulation is required such as in residential turfgrass applications.

Suspoemulsions are combinations of two active ingredients. One active ingredient is made as a suspension concentrate (1–50% active ingredient) and the second active is made as a emulsifiable concentrate (0.1 to 20%). A reason for making this kind of formulation is the inability to make an EC formulation of the first ingredient due to poor solubility in organic solvents. The suspoemulsion formulation allows for the combination of the two active ingredients to be packaged in one container, thereby minimizing packaging waste and giving greater convenience to the product user.

The herbicidal compounds of this invention may be formulated or applied with insecticides, fungicides, acaricides, nematicides, fertilizers, plant growth regulators or other agricultural chemicals. Certain tank mix additives, such as spreader stickers, penetration aids, wetting agents, surfactants, emulsifiers, humectants and UV protectants may be added in amounts of 0.01% to 5% to enhance the biological activity, stability, wetting, spreading on foliage or uptake of the active ingredients on the target area or to improve the suspensibility, dispersion, redispersion, emulsifiability, UV stability or other physical or physicochemical property of the active ingredient in the spray tank, spray system or target area.

Now, Formulation Examples of the present invention will be given as follows.

Formulation example 1. Emulsifiable Concentrate

| Ingredient Trade Name | Chemical Name | Supplier | Function | % wt./wt. |
|---|---|---|---|---|
| Compound No. B | | | Active Ingredient | 5.0 |
| Toximul H-A | Calcium sulfonate and nonionic surfactant blend | Stepan Co. | Emulsifier | 2.5 |
| Toximul D-A | Calcium sulfonate and nonionic surfactant blend | Stepan Co. | Emulsifier | 7.5 |
| Aromatic 200 | Aromatic hydrocarbon | Exxon Chemical Co. | Solvent | QS to 100% |

Formulation example 2. Suspension Concentrate

| Ingredient Trade Name | Chemical Name | Supplier | Function | % wt./wt. |
|---|---|---|---|---|
| Compound No.B | | | Active Ingredient | 10.00 |
| Propylene gylcol | | | Anti-freeze | 5.00 |
| Antifoam 1530 | Silicone defoamer | Dow Corning | Anti-foam | 0.50 |
| Rhodopol 23 | Xanthan gum | Rhone-Poulenc | Suspending Aid | 0.25 |
| Morwet D-425 | Napthalene formaldehyde condensate | Witco Corp. | Dispersant | 3.00 |
| Igepal CA-720 | Octylphenol ethoxylate | Rhone-Poulenc | Wetting agent | 3.00 |
| Proxel GXL | 1,2 benziso-thiazolin-3-one | ICI Americas | Preservative | 0.25 |
| Water | | | Diluent | 68.00 |

Formulation example 3. Wettable Powder

| Ingredient Trade Name | Chemical Name | Supplier | Function | % wt./wt. |
|---|---|---|---|---|
| Compound No.B | | | Active Ingredient | 50.00 |
| Geropon T-77 | Sodium-N-methyl-N-oleoyl taurate | Rhone-Poulenc | Wetting agent | 3.00 |
| Lomar PW | Napthalene Sulfonate | Henkel Corp. | Dispersant | 5.00 |
| Kaolin clay | Kaolin clay | J. M. Huber | Filler | 42.00 |

Formulation example 4. Water Dispersible Granule

| Ingredient Trade Name | Chemical Name | Supplier | Function | % wt./wt. |
|---|---|---|---|---|
| Compound No.B | | | Active Ingredient | 50.00 |
| Morwet EFW | | Witco Corp. | Wetting agent | 2.00 |
| Morwet D-425 | Napthalene formaldehyde condensate | Witco Corp. | Dispersant | 10.00 |
| ASP 400 | Kaolin Clay | Engelhard Corp. | Filler | 38.00 |

Compound B was applied to soil as a PRE emergent treatment at the rate of 250 g/ha. The broadleaf weed species velvetleaf (*Abutilon theophrasti*), redroot pigweed (*Amaranthus retroflexus*) and lambsquarters (*Chenopodium album*) were all 100% controlled by this treatment.

What is claimed is:

1. A process for producing 3-phenyl-2,4(1H,3H)-pyrimidinediones having the general formula (I) and their salts

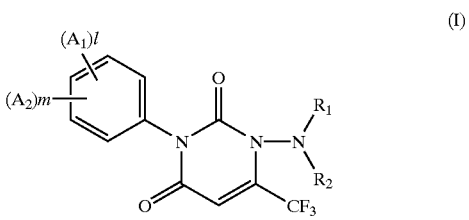

(I)

wherein $A_1$ is hydrogen, halogen, cyano, nitro, alkyl, alkenyl, alkynyl, cycloalkyl, cycloalkenyl, cyloalkynyl, cycloalkylalkyl, each being optionally substituted, $A_2$ is hydrogen, $-Q_1-A_3$ wherein $Q_1$ is O, S, SO, or $SO_2$; $A_3$ is hydrogen or $A_4$ ($A_4$ is alkyl, alkenyl, alkynyl, cycloalkyl, cycloalkenyl, cyloalkynyl, cycloalkylalkyl, aryl, arylalkyl, heterocyclyl, heterocyclicalkyl, each being optionally substituted), $-Q_1-CQ_2-A_3$ wherein $Q_2$ is O or S, $-Q_1-CQ_2-Q_2-A_3$, $-Q_1-CQ_2-N(A_3)_2$, $-CQ_2-A_3$, $-CQ_2-Q_2-A_3$, $-CQ_2-N(A_3)_2$, $-N(A_3)_2$, $-N(Q_1-A_3)_2$, $-N(CQ_2-A_3)_2$, $-N(Q_1-A_3)(CQ_2-A_3)$, $-N(CQ_2-Q_2-A_3)_2$, $-N(A_3)-CQ_2-N(A_3)_2$, or $-SO_2-N(A_3)_2$, each $A_3$ group of $(A_3)_2$ being independently same or different, any two of $(A_1)l$ and $(A_2)m$ groups being optionally combined through a saturated or unsaturated carbon, $-CQ_2-$, and/or hetero O, N, S, SO, or $SO_2$ linkage to form a cyclic ring having up to 12 membered ring, each being optionally substituted, $l$ is an integer of 1 to 5, m is an integer of 1 to 3, l+m is an integer of 2 to 5, $R_1$ is $A_4$, $-Q_1-A_3$, $-Q_1-CQ_2-A_3$, $-Q_1-CQ_2-Q_2-A_3$, $-Q_1-CQ_2-N(A_3)_2$, $-CQ_2-A_3$, $-CQ_2-Q_2-A_3$, $-CQ_2-N(A_3)_2$, $-N(A_3)_2$, $-N(Q_1-A_3)_2$, $-N(CQ_2-A_3)_2$, $-N(Q_1-A_3)(CQ_2-A_3)$, $-N(CQ_2-Q_2-A_3)_2$, $-N(A_3)-CQ_2-N(A_3)_2$, or $-SO_2-N(A_3)_2$, each $A_3$ group of $(A_3)_2$ being independently same or different, $R_2$ is hydrogen or $R_1$, $R_1$ and $R_2$ groups being optionally combined together with N of $N(R_1)(R_2)$ through a saturated or unsaturated carbon, $-CQ_2-$, and/or hetero O, N, S, SO, or $SO_2$ linkage to form a cyclic ring having up to 12 membered ring, each being optionally substituted, which comprises reacting an isocyanate represented by the general formula (II)

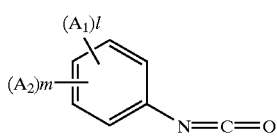

(II)

wherein $A_1$, $A_2$, l and m are as defined above, and a substituted hydrazono ester represented by the general formula (III)

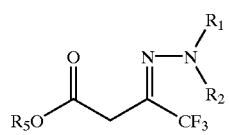

(III)

wherein $R_5$ is $A_4$, $R_1$ and $R_2$ are as defined above, with the presence of a Grignard reagent.

2. The process according to claim 1 for producing a 3-(3-substituted phenyl)-2,4(1H,3H)-pyrimidinedione having the formula (I-a) or its salt

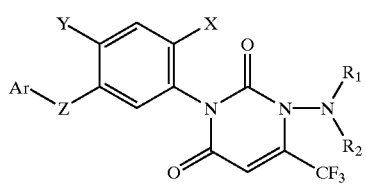

(I-a)

wherein

X, Y are hydrogen, halogen, cyano, nitro, alkyl, alkoxy, cycloalkyl, cycloalkylalkyl or thiocarbamoyl, each being optionally substituted, Z is O, S, SO, $SO_2$ or NR wherein R is alkyl, alkenyl, alkynyl, cycloalkyl, cycloalkylalkyl, each being optionally substituted, Ar is a substituted or unsubstituted 3 to 12 membered cyclic ring, it having optionally one or more saturated or unsaturated carbon, —$CQ_2$—, and/or hetero O, N, S, SO, or $SO_2$ linkage, $R_1$ is $A_4$, —$Q_1$—$A_3$, —$Q_1$—$CQ_2$—$A_3$, —$Q_1$—$CQ_2$—$Q_2$—$A_3$, —$Q_1$—$CQ_2$—$N(A_3)_2$, —$CQ_2$—$A_3$, —$CQ_2$—$Q_2$—$A_3$, —$CQ_2$—$N(A_3)_2$, —$N(A_3)_2$, —$N(Q_1$—$A_3)_2$, —$N(CQ_2$—$A_3)_2$, —$N(Q_1$—$A_3)$ ($CQ_2$—$A_3$), —$N(CQ_2$—$Q_2$—$A_3)_2$, —$N(A_3)$—$CQ_2$—$N(A_3)_2$, or —$SO_2$—$N(A_3)_2$, each $A_3$ group of $(A_3)_2$ being independently same or different, $R_2$ is hydrogen or $R_1$, $R_1$ and $R_2$ groups being optionally combined together with N of $N(R_1)(R_2)$ through a saturated or unsaturated carbon, —$CQ_2$—, and/or hetero O, N, S, SO, or $SO_2$ linkage to form a cyclic ring having up to 12 membered ring, each being optionally substituted, which comprises reacting an isocyanate represented by the general formula (II-a)

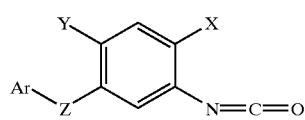

(II-a)

wherein Ar, X, Y, and Z are as defined above, and a substituted hydrazono ester represented by the formula (III-a)

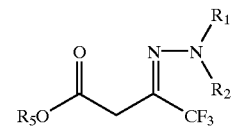

(III-a)

wherein $R_5$ is $A_4$.

3. A process according to claim 1 for producing a compound or its salt represented by the formula (I-c)

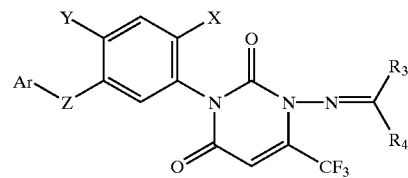

(I-c)

wherein

X, Y are hydrogen, halogen, cyano, nitro, alkyl, alkoxy, cycloalkyl, cycloalkylalkyl or thiocarbamoyl, each being optionally substituted, Z is O, S, SO, $SO_2$ or NR wherein R is alkyl, alkenyl, alkynyl, cycloalkyl, cycloalkylalkyl, each being optionally substituted, Ar is a substituted or unsubstituted 3 to 12 membered cyclic ring, it having optionally one or more saturated or unsaturated carbon, —$CQ_2$—, and/or hetero O, N, S, SO, or $SO_2$ linkage, $R_3$ is $A_4$, —$Q_1$—$A_3$, —$Q_1$—$CQ_2$—$A_3$, —$Q_1$—$CQ_2$—$Q_2$—$A_3$, —$Q_1$—$CQ_2$—$N(A_3)_2$, —$CQ_2$—$A_3$, —$CQ_2$—$Q_2$—$A_3$, —$CQ_2$—$N(A_3)_2$, —$N(A_3)_2$, —$N(Q_1$—$A_3)_2$, —$N(CQ_2$—$A_3)_2$, —$N(Q_1$—$A_3)$ ($CQ_2$—$A_3$), —$N(CQ_2$—$Q_2$—$A_3)_2$, —$N(A_3)$—$CQ_2$—$N(A_3)_2$, or —$SO_2$—$N(A_3)_2$, each $A_3$ of $(A_3)_2$ being independently same or different, $R_4$ is hydrogen or $R_3$, $R_3$ and $R_4$ groups being optionally combined together with C of =$C(R_3)(R_4)$ through a saturated or unsaturated carbon, —$CQ_2$—, and/or hetero O, N, S, SO, or $SO_2$ linkage to form a cyclic ring having up to 12 membered ring, each being optionally substituted, which comprises reacting an isocyanate represented by the formula (II-c)

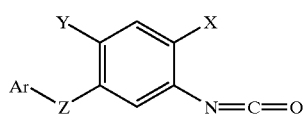

(II-c)

with a hydrazono-ester represented by the formula (III-c)

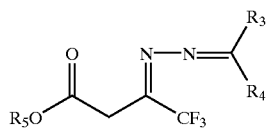

(III-)

wherein $R_5$ is $A_4$.

4. The process according to claim 1, wherein the reaction is carried out in the presence of tetrahydrofuran as the solvent.

5. The process according to claim 1, wherein the hydrazono-ester is alkyl 4,4,4-trifluoro-(3Z)-3-[(1-methylethylidene)hydrazono]-butanoate and the Grignard reagent is methyl magnesium bromide.

6. A compound or its salt represented by the formula (I-c)

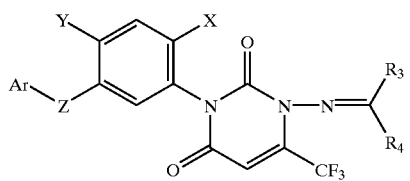

(I-c)

wherein

X, Y are hydrogen, halogen, cyano, nitro, alkyl, alkoxy, cycloalkyl, cycloalkylalkyl or thiocarbamoyl, Z is O, S, SO, $SO_2$ or NR wherein R is alkyl, alkenyl, alkynyl, cycloalkyl, or cycloalkylalkyl, Ar is pyridyl, pyrimidyl, triazolyl, thiazolyl, isothiazolyl, or phenyl, or pyridyl, pyrimidyl, triazolyl, thiazolyl, isothiazolyl, or phenyl substituted with up to five substituents independently selected the from group consisting of bromo, chloro, fluoro, iodo, $(C_1-C_4)$alkyl, halo$(C_{1-4})$alkyl $C_{1-4}$)alkoxy, $(C_{1-4})$alkylthio, halo$(_{C1-4})$ alkoxy, $(C_{1-4})$alkylsulfonyl, $(C_1-C_3)$alkylsulfinyl, di$(C_{1-4})$alkylaminocarbonyl, cyano, nitro, $(C_{1-4})$ alkylsulfonylamino, $(C_{1-4})$alkoxycarbony$(C_{1-4})$alkoxy, and $(C_{1-4})$alkoxycarbonylamino, $R_3$ is $A_4$, —$Q_1$—$A_3$, —$Q_1$—$CQ_2$—$A_3$, —$Q_1$—$CQ_2$—$Q_2$—$A_3$, —$Q_1$—$CQ_2$—$N(A_3)_2$, —$CQ_2$—$A_3$, —$CQ_2$—$Q_2$—$A_3$, —$CQ_2$—$N(A_3)_2$, —$N(A_3)_2$, —$N(Q_1$—$A_3)_2$, —$N(CQ_2$—$A_3)_2$, —$N(Q_1$—$A_3)$ $(CQ_2$—$A_3)$, —$N(CQ_2$—$Q_2$—$A_3)_2$, —$N(A_3)$—$CQ_2$—$N(A_3)_2$, or —$SO_2$—$N(A_3)_2$, each $A_3$ of $(A_3)_2$ being independently same or different, $R_4$ is hydrogen or $R_3$, $R_3$ and $R_4$ groups being optionally combined together with C of =C($R_3$)($R_4$) to form a cyclopentylidene.

7. The compound or its salt according to claim 6, wherein

X is fluorine, and

Y is chlorine, and

Z is oxygen or sulfur, and

Ar is 2-pyridyl, 3-pyridyl, 4-pyridyl, 3-bromo-2-pyridyl, 5-bromo-2-pyridyl, 6-bromo-2-pyridyl, 3-chloro-2-pyridyl, 5-chloro-2-pyridyl, 6-chloro-2-pyridyl, 3-fluoro-2-pyridyl, 5-fluoro-2-pyridyl, 6-fluoro-2-pyridyl, 3-cyano-2-pyridyl, 5-cyano-2-pyridyl, 6-cyano-2-pyridyl, 3-nitro-2-pyridyl, 5-nitro-2-pyridyl, 6-nitro-2-pyridyl, 3-trifluoromethyl-2-pyridyl, 4-trifluoromethyl-2-pyridyl, 5-trifluoromethyl-2-pyridyl, 6-trifluoromethyl-2-pyridyl, 3-dimethylaminocarbonyl-2-pyridyl, 3-methylsulfonyl-2-pyridyl, 3-isopropylsulfonyl-2-pyridyl, 6-chloro-3-trifluoromethyl-2-pyridyl, 3,5,6-trifluoropyridyl, 2-pyrimidyl, 4-pyrimidyl, 5-bromo-2-pyrimidyl, 4-chloro-2-pyrimidyl, 4-trifluoromethyl-2-pyrimidyl, 4,6-dimethoxy-2-pyrimidyl, 2,6-dimethoxy-4-pyrimidyl, 4,6-dimethoxy-2-triazinyl, phenyl, 2-iodophenyl, 2-trifluoromethoxyphenyl, 2-nitrophenyl, 4-nitrophenyl, 4-methylsulfonylaminophenyl, 4-(1-ethoxycarbonylethoxy)phenyl, 2-cyanophenyl, 2-cyano-3-fluorophenyl, 2-cyano-4-fluorophenyl, 2-cyano-4-nitrophenyl, 4-nitro-2-trifluoromethylphenyl, 4-acetylamino-2-trifluoromethylphenyl, 4-(1-ethoxycarbonylethoxy)-2-nitrophenyl, 5-chloro-4-(1-ethoxycarbonylethoxy)-2-nitrophenyl, 3-methyl-4-nitro-5-isothiazolyl, or 5-nitro-2-thiazolyl.

8. A herbicidal composition comprising an effective amount of one or more compounds selected from claim 6 in combination with an inert carrier.

* * * * *